United States Patent [19]
Berman et al.

[11] Patent Number: 5,669,921
[45] Date of Patent: Sep. 23, 1997

[54] ENDOSCOPIC SHAVER BLADE WINDOW POSITIONING SYSTEM

[75] Inventors: Phillip J. Berman, St. Petersburg; Raymond A. Carr, Clearwater Beach, both of Fla.

[73] Assignee: Linvatec Corporation, Largo, Fla.

[21] Appl. No.: 617,524

[22] Filed: Mar. 15, 1996

Related U.S. Application Data

[63] Continuation-in-part of Ser. No. 276,979, Jul. 19, 1994, abandoned.

[51] Int. Cl.$^6$ ............................................. A61B 17/32
[52] U.S. Cl. .............................. 606/167; 606/170
[58] Field of Search ........................... 606/170, 167, 606/168, 171, 174, 180

[56] References Cited

U.S. PATENT DOCUMENTS

| | | |
|---|---|---|
| 4,200,106 | 4/1980 | Douvas et al. . |
| 4,705,038 | 11/1987 | Sjostrom et al. . |
| 5,077,506 | 12/1991 | Krause . |
| 5,269,798 | 12/1993 | Winkler ................................ 606/170 |
| 5,286,253 | 2/1994 | Fucci .................................... 606/170 |

OTHER PUBLICATIONS

Intraarc 9963 Drive System Instruction Guide and Service Manual, Linvatec Corporation, 1991, 4 pages.
Concept Arthroscopy Products Catalog 1992, Linvatec Corporation, Intraarc 9963 Arthroscopy Power System, 3 pages.

*Primary Examiner*—Michael Buiz
*Assistant Examiner*—Kevin Truong
*Attorney, Agent, or Firm*—Gene Warzecha

[57] ABSTRACT

A positioning system for controlling the orientation of the movable elongated inner member relative to the fixed elongated outer member of a surgical instrument. An endoscopic rotatable shaver instrument incorporates a shaver blade assembly adapted to be received in and driven by a handpiece. The movable component of the shaver blade assembly is provided with a position indicator which is read by a sensor in the handpiece in order to control the position at which the inner member is stopped relative to the outer member. The invention is embodied in an apparatus and method enabling use of a shaver blade assembly as an aspirating device or as a probe without any aspirating function.

8 Claims, 4 Drawing Sheets

ENDOSCOPIC SHAVER BLADE WINDOW POSITIONING SYSTEM

This application is a continuation-in-part of application Ser. No. 08/276,979 filed Jul. 19, 1994, now abandoned.

BACKGROUND OF THE INVENTION

1. Field of the Invention

The invention relates to powered surgical tissue removal devices. More particularly, the invention relates to an endoscopic surgical shaver in which an elongated hollow inner tube having a cutting distal tip is axially situated within and moves relative to an elongated hollow outer tube having a distal window in order to achieve a tissue resection at the distal tip of the combined inner/outer shaver assembly. Still more particularly, the invention relates to a system and method for controlling the relative positions of the inner and outer tubes to selectively control the size of the cutting window.

2. Description of the Prior Art

The use of elongated surgical resecting instruments has become well accepted in performing closed surgery such as arthroscopic or, more generally, endoscopic surgery. In closed surgery, access to the surgical site is gained via one or more portals in the body, and instruments and cameras (scopes) used in the surgical procedure must be elongated to permit the distal ends of the instruments and cameras to reach the surgical site. Some conventional surgical resecting instruments (shavers) for use in closed surgery are powered and have a straight, elongated outer tubular member and a straight, elongated inner tubular member concentrically disposed in the outer tubular member. The inner and outer members both separately and jointly are sometimes referred to in the art as "blades" and are usually disposable. The outer member has a distal end having an opening in the end or side wall (or both) to form a cutting port or window and the inner member has a distal end disposed adjacent the opening in the distal end of the outer member. The inner member is (usually) easily insertable into and removable from the outer member to facilitate cleaning or interchanging parts. Each of the elongated members has a hub or termination at its proximal end in order to attach the components to a rotary (or linear) drive means within a reusable handpiece. The distal end of the inner tubular member has a cutting means or cutting edge for engaging tissue via the opening in the distal end of the outer tubular member. In many cases (but not all) this distal cutting means cooperates with the opening in the outer member to shear, cut, or trim tissue. In some cases, such as abrading burrs, the opening in the outer member merely allows access to the tissue and does not otherwise cooperate with the cutting means. Some soft tissues are not able to be effectively resected in this manner because they do not resist deflection and, therefore, not enough shear force can be developed to initiate a cut. The terms "cutting edge", "cutting means", "resecting means", etc. as used herein are intended to include abrading (e.g. burrs) and other devices whether or not there is any traditional cutting or shaving action and whether or not there is any cooperative shearing action. The inner tubular member is rotatably driven about its axis from its proximal end, normally via a small electric or pneumatic motor in the handpiece which is controlled by either finger actuated switches or levers on the handpiece, a foot switch or switches on a console supplying power to the handpiece. The distal ends of the various styles of inner tubular members can have various configurations depending upon the surgical procedure to be performed, and the opening in the distal end of the outer tubular member would then have a configuration adapted to cooperate with the particular configuration of the distal end on the inner tubular member. For example, the inner and outer tubular members can be configured to produce whisker cutting, lipectomy, polypectomy, synovial resection, arthroplasty burring or abrading, side cutting, meniscus cutting, trimming, full radius resection, end cutting and the like, and the various configurations are referred to generically as cutting means.

The aforementioned elongated surgical cutting instruments are available in angled configurations in which the axes of the distal tips of the inner and outer members are aligned and offset or bent at a fixed or variable angle relative to the axes of the proximal ends of the aligned inner and outer members. The inner member of the angled devices usually has a hollow plastic body or metal coil and a metallic distal tip into which a cutting edge is formed. In all of these devices, the loose tissue resulting from the cutting, resecting or abrading procedure may be aspirated through the hollow, axially aligned lumen in the interior of the inner tubular member to be collected via a vacuum tube communicating with the handpiece. The entry to this lumen is through the cutting window which is the opening at the distal ends of the elongated tubes. The devices are generally used to cut and aspirate simultaneously or intermittently since the surgical site is usually distended by some fluid medium.

In conventional systems, the aspiration occurs intermittently through the cutting window during use because the oscillating, rotating or reciprocating motion of the instrument only cyclically opens the interior lumen in many blade designs. It occasionally becomes necessary during a surgical procedure to temporarily stop the cutting action of the shaver assembly in order to leave the lumen aperture open to allow the aspiration of fluid and debris to continue until the debris is sufficiently clear to improve the visualization. However, this is not always easy since known systems randomly stop the motion of the inner member relative to the outer member so that the size of the opening at the distal tip of the assembly, i.e. the entry of the inner lumen or lumen aperture, is unpredictable. It would be advantageous to control the position at which the motion of the inner member is stopped so that the size of the aperture could be controlled to improve the efficiency of aspiration during those times when the surgeon wants to use the shaver assembly for aspiration only. Such control would also enable the inner member to be stopped in a closed position to prevent aspiration and permit use of the shaver as a simple probe, thus limiting the need to use other instruments.

During certain surgical procedures (e.g. spinal; ear, nose, throat or ENT; etc.) there is no fluid medium surrounding the work site and it may be desirable to introduce irrigating fluid to the surgical site in order to simply irrigate the site to improve visualization and to facilitate the aspiration of debris. Such irrigation is usually provided by separate instruments generally known as irrigation/aspiration devices which can be used to either irrigate or aspirate a site. However, irrigation could easily be provided through the lumen of the inner member (with suitable check valves, etc.) provided the size of the distal opening could be controlled in a known manner.

It is an object of this invention to produce a surgical shaver system in which the position of the inner member relative to the outer member may be monitored.

It is also an object of this invention to produce a shaver system in which the inner member may be stopped at a predetermined position in order to produce a known size window opening or aperture at the distal tip of the assembly.

It is yet another object of this invention to produce a surgical tissue resecting instrument which may be easily changed from one mode of operation (e.g. resecting with aspiration) to another (e.g. probe with no aspiration).

SUMMARY OF THE INVENTION

These and other objects of this invention are achieved by the preferred embodiment disclosed herein which is a surgical resection system comprising a handpiece for driving a surgical instrument by means of a motor within the handpiece. The handpiece is adapted to receive an instrument comprising an elongated outer tube having a proximal end, a distal end, an outer member opening at the distal end and a hub at the proximal end. The hub enables attachment of the outer tube to the handpiece. An elongated inner tube is movably received in the outer tube and has a proximal end, a distal end, an inner member opening at the distal end and with a cutting edge at the opening to cut tissue and a hub at the proximal end. The hub enables attachment of the inner tube to the motor. An indicator means is secured to the inner tube at a predetermined angular position relative to the inner member opening. A sensing means for sensing the indicator means is provided on the handpiece and a control means responsive to the sensor means acts to control the motor to position the inner member opening in a predetermined angular position relative to the outer predetermined opening when rotation of said inner member is stopped.

The invention also resides in a method for performing a surgical procedure comprising the steps of providing a shaver assembly having an elongated outer tube and an elongated inner tube for being rotated in the outer tube. A cutting edge at an opening at the distal end of the inner tube cooperates with an opening at the distal end of the outer member to cut tissue. The method further comprises providing an indicator means on the inner tube at a predetermined angular position relative to the inner member opening, sensing the angular position of the indicator means relative to the outer opening, selecting a predetermined size opening at the distal end of the outer tube and stopping the motion of the inner member relative to the outer member to produce the predetermined size opening.

DESCRIPTION OF THE PREFERRED EMBODIMENT

Figure 1:
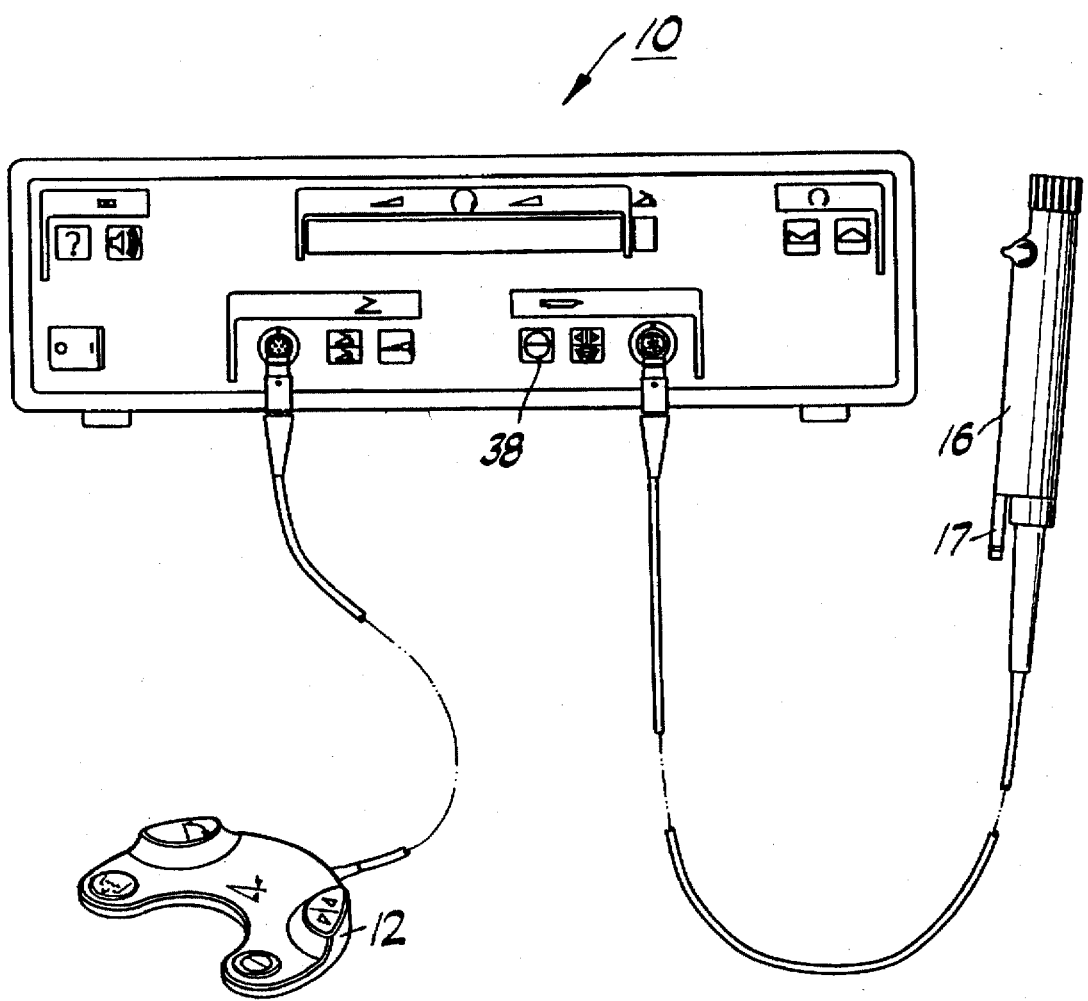
FIG. 1 is a diagrammatic view of a prior art endoscopic resecting system.

Referring now to FIG. 1, there is shown a diagrammatic representation of a prior art surgical cutting system 10 designed primarily for controlling rotatable, motor driven endoscopic shaver assemblies. The invention is equally applicable to any endoscopic motor driven cutting type device. The term "drive" as used herein simply means one part of a system is moved relative to another. System 10 comprises foot switch 12, console 14 and handpiece 16. A prior art drive system and a handpiece are described in U.S. Pat. No. 5,269,794 (Rexroth) assigned to the assignee hereof and incorporated by reference herein. Handpiece 16 is designed to selectively receive any one of a variety of endoscopic or arthroscopic surgical instruments, each comprising a rotatable elongated inner member situated within a fixed elongated outer member. Cutting edges at the distal end of the inner member serve to resect or abrade tissue during endoscopic surgical procedures, the debris being removed from the surgical site through the lumen of the inner member via an aspirating suction port 17 as will be understood by those skilled in the art.

As used herein, the term "blades" means any cutting device operated by system 10 including rotatable or otherwise movable blades, burrs, etc. Console 14 incorporates several conventional control buttons on its front panel although only control button 38, the purpose of which will be discussed below, is associated with the invention.

Figure 2:
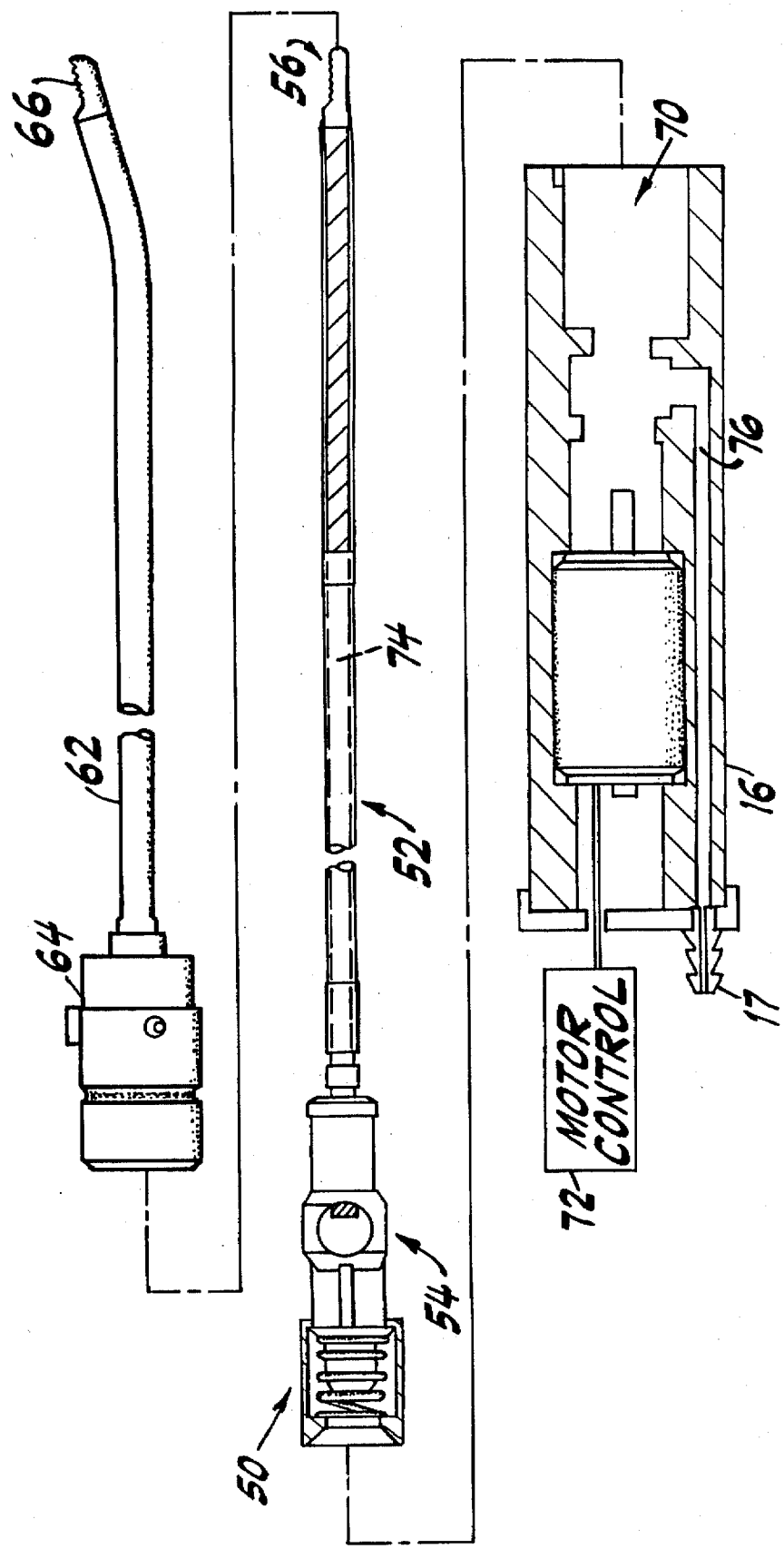
FIG. 2 is an exploded view, partly in cross-section, of a prior art handpiece and associated surgical shaver assembly.

An exploded diagrammatic view of handpiece 16 is shown in FIG. 2 with an associated shaver blade assembly 50 comprising an elongated inner tubular member 52, having a hub 54 and a distal cutting edge 56, and an elongated outer tubular member 62 having a proximal hub 64 and a distal opening 66. FIG. 2 shows a prior art, angled shaver blade assembly more particularly described in U.S. Pat. No. 5,286,253 (Fucci), assigned to the assignee hereof and incorporated by reference herein. The inner member 52 and outer member 62 are assembled and received in aperture 70 of handpiece 16. Rotation of inner member 52 is controlled by motor control 72 and aspiration of fluid and debris occurs through lumen 74 and channel 76 when port 17 is connected to a suction source (not shown). It will be understood that the interior of the inner member is open to the ambient at distal edge 56. This opening is herein referred to as the lumen aperture and its size varies according to the rotation of the inner member as cutting edge 56 cyclically covers and uncovers outer window 66.

Figure 3:
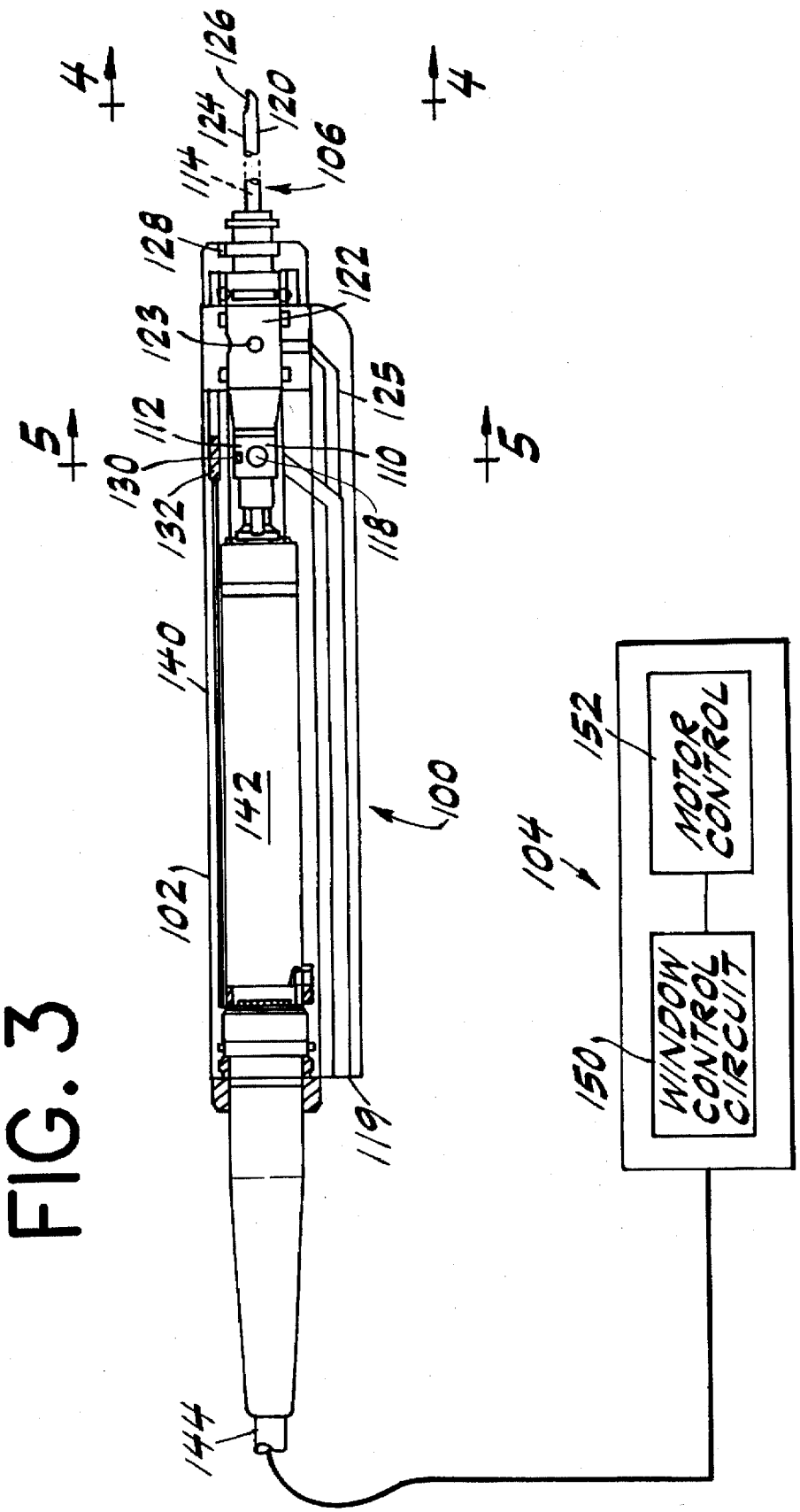
FIG. 3 is a diagrammatic view, partly in cross-section, of an endoscopic shaver incorporating a window positioning system according to the principles of this invention.
Figure 4:
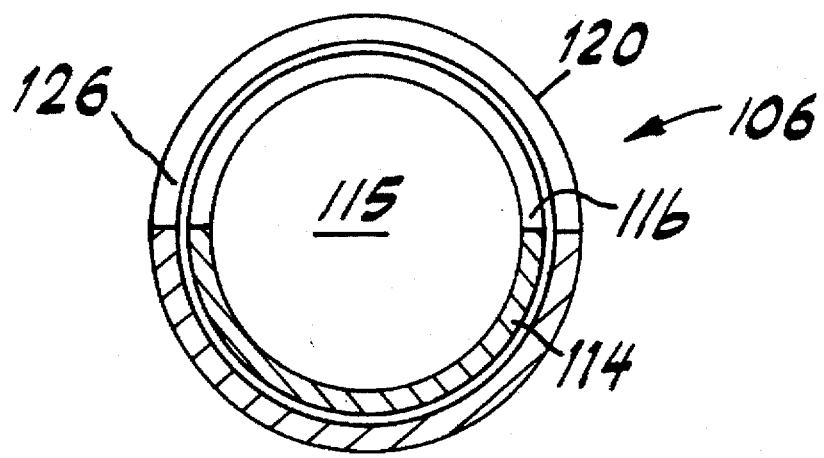
FIG. 4 is a sectional view of FIG. 1 taken along the lines 4—4.
Figure 5:
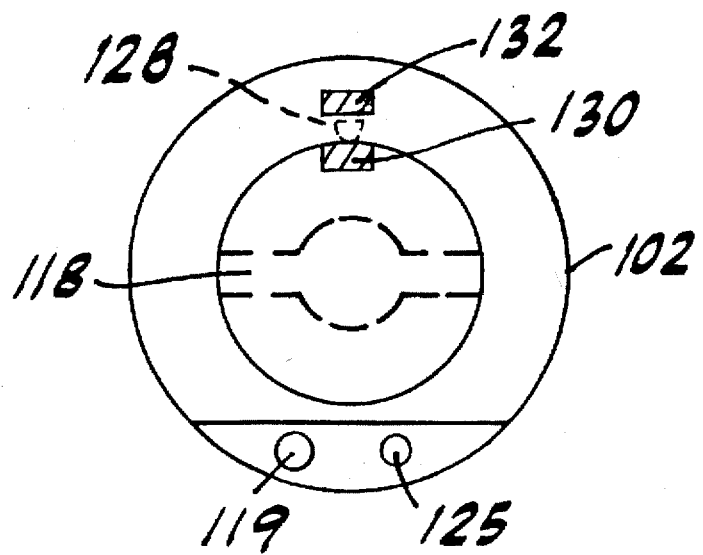
FIG. 5 is a sectional view of FIG. 1 taken along the lines 5—5.

Referring now to FIGS. 3–5, a modification of prior art system 10 is shown as system 100 comprising a handpiece 102 controlled by control system 104 and adapted to receive an elongated shaver blade assembly 106. The latter comprises an elongated inner member 110 having a proximal hub 112, an elongated tubular body 114 with a central lumen 115 and a cutting opening 116 at its distal end. Inner member 110 includes an aspiration aperture 118 in hub 112 which is in communication with lumen 115 and aspirating channel 119 associated with the handpiece body. The inner member is received in elongated outer member 120 having a proximal hub 122, an elongated body 124 and a distal opening 126. As in the prior art system, the lumen aperture size varies. The outer member also comprises an optional irrigation port 123 in proximal hub 122 in communication with an irrigating channel within the blade assembly (not shown) and channel 125 associated with the handpiece body. The proximal hub 122 of the outer member is provided with a key 128 which is received within a corresponding aperture (not shown) in the distal end of handpiece 110 in order to fix the angular orientation of outer opening 126. A window positioning system is provided, as will be understood below, to enable positioning of the inner cutting opening 116 relative to outer window 126. Key components of this system are indicator 130 situated on the movable, proximal hub 112 and sensor 132 fixed on the interior of the handpiece. Indicator 130 is placed in a known angular position relative to opening 116 of the inner member. When the shaver blade assembly is properly inserted in the handpiece, indicator 130 may be adjacent sensor 132 as shown in FIG. 3. The sensor may be positioned in a variety of locations (e.g. hub, tubular member, etc.) so long as it is fixedly secured relative to the outer distal opening 126.

Handpiece 102 comprises a body 140 having a conventional motor means 142 joined by cable 144 to control system 104. Control system 104 comprises, in addition to conventional subassemblies required to operate the shaver blade assembly, a window control circuit 150 which is responsive to sensor 132 in order to provide suitable signals to motor control 152 to drive the motor output so as to position inner member 114 as desired. Activation of control system 104 to stop the inner member in a desired position may be achieved by an "aspirate" button 38 on control panel 14 or on foot switch 12.

As shown in FIG. 4, the inner and outer openings 116 and 126 may be stopped fully open, i.e. in alignment, to maximize the lumen aperture. Any size opening is achievable between fully open and fully closed.

In the preferred embodiment, indicator 130 is a magnet subtending a small arcuate distance on the surface of hub 112 as best seen in FIG. 5. Alternatively, the indicator could be embedded within the hub and/or could be a variety of other devices such as a ferrous metal plug, a bar code, an optical device such as a reflective stripe, an electrical contact, etc. Sensor 132 may be a reed switch, Hall-effect sensor, laser source with fiber optic receiver, eddy current sensor, electrical contact or other sensor which is responsive to the particular indicator to produce a signal representative of the angular orientation of the window at the distal end of the inner member. While only one indicator 130 is shown, it is in angular alignment with (or at least in a known angular relationship to) the inner opening. Clearly, a separate or additional indicator (not shown) could be provided elsewhere on the inner member. For example, an indicator could be provided to face sensor 132 when the lumen aperture is closed.

One may envision numerous configurations adapted to achieve the goals of the present invention. One such system is disclosed in the co-pending parent application hereof (incorporated by reference). For example, the control system may continually monitor the position of the inner member so that at any point in time when a signal is received to stop the motor, the control system may delay the actual stop (by no more than one rotation) until the sensor on the inner member is directly opposite the indicator means. Alternatively, the control system may simply monitor the position of the indicator means once per revolution so that when a stop signal is received, the motor speed could be automatically decreased from several thousand rpm to a very slow speed on the order to 1–10 rpm so that upon the next occurrence of the indicator means being opposite the sensor means the motor could be immediately automatically stopped. The control system could also be adapted to work with a stepper motor and to count motor pulses per revolution so the motor could be stopped when desired, either automatically when a certain reference point is reached or manually under visualization of the lumen aperture through an arthroscope (endoscope).

While the preferred embodiment disclosed has been presented in the form of a rotatable system, it should be understood that the invention is adaptable to other systems in which the inner member moves relative to the outer in some other fashion (e.g. reciprocal motion). Thus, a system utilizing longitudinally reciprocating motion of the inner member may be adapted to control the size of the window opening.

It will be understood by those skilled in the art that numerous improvements and modifications may be made to the preferred embodiment of the invention disclosed herein without departing from the spirit and scope thereof.

What is claimed is:

1. A method for performing a surgical procedure with a rotatable shaver driven by a powered handpiece having a drive means for driving said shaver comprising the steps of:
   providing a shaver assembly comprising:
      an elongated outer tube having a proximal end, a distal end, an outer opening at said distal end and a hub at said proximal end, said hub for enabling attachment of said outer tube to said handpiece; and
      an elongated inner tube, for being received in said outer tube, having a proximal end, a distal end, an inner opening at said distal end, a cutting edge at said inner opening for cooperating with said outer opening to cut tissue and a hub at said proximal end, said hub for enabling attachment of said inner tube to said drive means, said inner and outer openings cooperating to produce a lumen aperture of cyclically varying size;
      an indicator means secured to said hub of said inner tube at a predetermined angular position relative to said inner opening;
   sensing the angular position of said indicator means relative to said outer opening;
   selecting a predetermined angular position of said indicator means representative of a predetermined size opening of said lumen aperture;
   stopping the motion of said inner tube relative to said outer tube to produce said predetermined size opening.

2. A method according to claim 1 further comprising the steps of:
   selecting a maximum lumen aperture to facilitate utilizing said shaver assembly as an aspirator only.

3. A method according to claim 1 further comprising the steps of:
   selecting a minimum lumen aperture to facilitate utilizing said shaver assembly as a probe.

4. A method for performing a surgical procedure with a powered surgical resecting instrument driven by a powered handpiece having a drive means for driving said instrument comprising the steps of:
   providing a surgical instrument assembly comprising:
      an elongated outer tube having a proximal end, a distal end, an outer opening at said distal end and a hub at said proximal end, said hub for enabling attachment of said outer tube to said handpiece; and
      an elongated inner tube, for being received in said outer tube, having a proximal end, a distal end, an inner opening at said distal end, a cutting edge at said inner opening for cooperating with said outer opening to cut tissue and a hub at said proximal end, said hub for enabling attachment of said inner tube to said drive means, said inner and outer openings cooperating to produce a lumen aperture of cyclically varying size;
      an indicator means secured to said inner tube at a predetermined angular position relative to said inner opening;
   sensing the angular position of said indicator means relative to said outer opening;
   selecting a predetermined angular position of said indicator means representative of a predetermined size opening of said lumen aperture;
   stopping the motion of said inner tube relative to said outer tube to produce said predetermined size opening.

5. A method of controlling a powered surgical instrument having an elongated inner member movable relative to a stationary elongated outer member, said outer member having a distal cutting window and said inner member having a cutting means which cyclically covers said cutting window comprising the steps of:

placing an indicator on the movable element;

placing a sensor on the stationary element, said sensor responsive to said indicator;

sensing the position of said cutting window relative to said cutting means;

stopping the movable element in a predetermined position relative to the stationary element.

6. A method of controlling the speed of rotation of a rotatable surgical shaver having a rotatable elongated inner member within a fixed elongated outer member, said outer member having a distal cutting window and said inner member having a cutting means which cyclically covers said cutting window comprising the steps of:

adjusting the speed of rotation of the inner member to a predetermined slow rate;

monitoring the size of the said window opening at the distal end of said shaver;

stopping the rotation of said inner member at a predetermined point thereby creating a predetermined size window opening.

7. A method according to claim 6 wherein said predetermined slow rate is approximately one revolution per second.

8. A method according to claim 6 wherein said monitoring is done visually via an arthroscope.

* * * * *